(12) United States Patent
Brown

(10) Patent No.: US 6,168,429 B1
(45) Date of Patent: Jan. 2, 2001

(54) ORTHODONTIC BRACKET INSERT

(75) Inventor: William Burns Terrell Brown, Ponte Vedra Beach, FL (US)

(73) Assignee: Jelaga Incorporated, Jasper, MI (US)

( * ) Notice: Under 35 U.S.C. 154(b), the term of this patent shall be extended for 0 days.

(21) Appl. No.: 09/414,577

(22) Filed: Oct. 9, 1999

(51) Int. Cl.[7] ........................................... A61C 3/00
(52) U.S. Cl. ................................... 433/11; 433/13
(58) Field of Search ........................... 433/10, 11, 13, 433/14, 17, 22

(56) References Cited

U.S. PATENT DOCUMENTS

| | | |
|---|---|---|
| 2,019,773 | 11/1935 | Wirt . |
| 3,128,552 | 4/1964 | Broussard . |
| 3,391,461 * | 7/1968 | Johnson ................................. 433/17 |
| 3,505,736 * | 4/1970 | Brader et al. ........................... 433/14 |
| 3,729,826 * | 5/1973 | Kesling .................................. 433/13 |
| 4,103,423 * | 8/1978 | Kessel ..................................... 433/14 |
| 4,355,975 * | 10/1982 | Fujita ...................................... 433/11 |
| 4,551,094 * | 11/1985 | Kesling .................................. 433/17 |
| 4,712,999 * | 12/1987 | Rosenberg .............................. 433/11 |
| 5,094,614 | 3/1992 | Wildman . |
| 5,439,378 | 8/1995 | Damon . |
| 5,630,715 | 5/1997 | Voudouris . |
| 5,738,513 * | 4/1998 | Hermann ................................ 433/13 |
| 5,908,293 * | 6/1999 | Voudouris .............................. 433/11 |

* cited by examiner

Primary Examiner—Todd E. Manahan
(74) Attorney, Agent, or Firm—Young & Basile, P.C.

(57) ABSTRACT

An insert for generic or custom preadjusted edgewise brackets. The device is formed of metallic material or synthetic material, or resilient elastomeric material. The device will capture and retain the orthodontic archwire into the archwire slot of the orthodontic edgewise bracket. The device includes a region aligned with the archwire slot in the edgewise bracket to position, but not frictionally interfere with the archwire, because it does not put pressure on the archwire, but creates a tunnel for the archwire to easily slide through. The crescent shaped horizontal anchors defined on the device cooperate with the underside of the tiewings on the edgewise bracket to maintain the device in position. The crescent shape provides room for other ancillary devices to be placed on the bracket and secured behind the tiewings when the device is in place. The laterally extending wings covering and extending beyond the archwire slot also provide increased rotational control of the teeth, and act as a sheath over the archwire so that ancillary devices when placed on the bracket will not create friction. The device is placed on the edgewise brackets or removed at the discretion of the dental practitioner.

14 Claims, 4 Drawing Sheets

ORTHODONTIC BRACKET INSERT

BACKGROUND OF THE INVENTION

1. Field of the Invention

The invention pertains to orthodontic brackets, and in particular, to twin edgewise orthodontic bracket inserts employed to maintain the archwire in the proper relationship to the bracket.

2. Description of the Related Art

Orthodontics is that field of dentistry which deals with changing the position of the teeth within each dental arch as well as the fit of the teeth in each dental arch against the opposing teeth. When teeth are not in the correct position, the resulting condition is termed malocclusion. Malocclusions may result from jaw shape, position, or size discrepancies. For example, the upper jaw may be too narrow in width as compared to the lower jaw, resulting in an incorrect fit of the lower teeth against the upper teeth. Or, the jaw size may be too small in comparison to the tooth sizes, resulting in crowding, which affects both alignment of the teeth within the same arch and the fit of the teeth in each arch against the opposing teeth as the jaws close together.

Tooth position changes are accomplished by the application of carefully calibrated mechanical forces applied by mechanisms attached to the patient's teeth. Generally, these mechanisms are comprised of precisely engineered brackets cemented to the surface of each tooth and a small diameter resilient wire (the archwire) that is attached to each bracket with a ligature. As the resilient wire is deflected from its original shape by being tied with the ligature into a slot within each bracket (the archwire slot), it applies force to the teeth as it attempts to rebound to its original form. The biologic system of the patient responds to this applied force with cellular alterations that allow the position of the teeth to change. For the desired movement to occur, the archwire and ligature must not only provide the motive forces, but also must allow the brackets to slide along the archwire. Binding of the bracket slot against the archwire (friction) alters the dynamic of forces at work within the mechanism, confuses the biologic response and disrupts the smooth flow of the treatment process.

In 1928, Edward H. Angle, the father of modern orthodontics, introduced the Edgewise Bracket. While orthodontic brackets have evolved since 1928 into a myriad of shapes and designs, Angle's edgewise bracket and its variations still comprise the vast majority of orthodontic brackets used today. The edgewise bracket such as that shown in FIG. 1 includes a translateral, horizontal slot that is rectangular in cross-section with an open face that allows insertion of the archwire. The open face allows for a more convenient placement of the wire, as opposed to threading the wire through an enclosed tube. The open face also allows the wire to be adjusted to apply individualized forces to each specific tooth. The rectangular slot provides a mechanism for applying a twisting force to each tooth if a rectangular wire is used. As the rectangular wire rotates, its edges (hence the term edgewise) engage the walls of the slot, providing the clinician the ability to control movement of each tooth in all three planes of space, i.e. vertical, horizontal and rotational. The tiewings provide a secure support and attachment for the ligatures, which hold the archwire into the slot by passing over the archwire as it exits each side of the slot. The double tiewings provide exceptional rotational control over a single tiewing design.

Ligation of the archwire, while necessary to hold the archwire into the slot, adds significantly to the friction of the system. Friction impedes the smooth movement of the archwire through the edgewise bracket and the sliding of the teeth along the archwire. Friction requires an increase in the applied levels of force and reduces the efficiency of the mechanism by creating rapid decay of the applied forces. In practical terms, force decay requires the mechanism to be reactivated more often so the practitioner must see patients at time intervals that could otherwise be much longer. The financial implications of this phenomenon are clear.

Nevertheless, the twin edgewise bracket continues to be the most popular orthodontic bracket used today. The design has been adapted over the years with preadjustments manufactured in the edgewise slot to increase efficiency and improve the result. Other design adaptations have changed the outside shape of the tiewings to a rhomboid to effect better bracket placement, among other things. Several edgewise brackets have been designed with caps, lids, slides or locks that capture the archwire in the archwire slot. These mechanisms overcome the friction problem by eliminating the need for ligatures. In each of these designs, the basic twin edgewise, or single edgewise shape, has been altered to accept the cap, lid, slide or lock. In other words, in each of the designs, the individual edgewise bracket is altered to receive the cap, lid, slide or lock, and the design consists of both pieces, the custom bracket and the custom cap, lid, slide or lock.

OBJECTS OF THE INVENTION

It is an object of the invention to provide an orthodontic bracket insert which fits between the tiewings of a conventional twin edgewise bracket and the overall insert construction is substantially concentric with respect to the configuration of the bracket tiewings.

A further object of the invention is to provide an orthodontic bracket and insert assembly which permits the insert to be located above an archwire located in the bracket slot without binding the archwire in any manner.

Another object of the invention is to provide an orthodontic bracket and insert wherein extensions are defined upon the insert to be located under and concentric to the underside of the tiewings to insure that the insert is firmly anchored, and the need for a ligature is eliminated.

Another object of the invention is to provide an orthodontic bracket and insert wherein the extensions are defined upon the insert to be located under and concentric to the underside of the tiewings and to provide enough additional space to allow the anchoring of another ancillary device on top of this device.

Another object of the invention is to provide an orthodontic bracket and insert assembly wherein the insert includes positioning stops or shoulders which permit the insert to be accurately located over the archwire slot to prevent the insert from binding with respect to the archwire.

An additional object of the invention is to provide an orthodontic bracket and insert assembly wherein the horizontal sleeves from the main body of the device cover the archwire slot and extend beyond the slot. These sleeves afford excellent rotational control of the tooth, and provide a rest for other ancillary products anchored to the bracket by way of a ligature. The rest does not allow the ancillary device to touch the archwire, therefore it eliminates binding.

SUMMARY OF THE INVENTION

The bracket with which the insert of the invention is utilized is of a generally conventional nature having a pad body concave roughened support surface which engages the tooth, or the body is welded or brazed to a bonding pad which engages the tooth. The longitudinal length of the pad body defines an axis and tiewings extend laterally from the body in opposite directions from the axis and define an archwire receiving slot therebetween. The tiewings include extensions extending beyond the lateral sides of the pad body, and the underside of such extensions are utilized by the insert anchors in accord with the invention to maintain the insert assembled on the bracket body.

The insert retainer includes a central portion adapted to overlie the bracket archwire slot, and this central portion includes shoulders or abutments which will maintain the insert central portion in a predetermined spaced and superimposed relationship with respect to the archwire which does not produce binding.

The insert or retainer is maintained upon the bracket by anchors defined upon the lateral sides of the insert. Depending upon the material of which the retainer is formed, such anchors may take the form of elongated crescent shaped extensions having end portions wherein the end portions engage the underside of the tiewings, or the insert anchors may consist of a pair of laterally extending resilient fingers, each having a knob or protuberance defined thereon for engaging with the tiewing undersides to maintain the retainer in position, or the retainer anchors may take the form of deformable fingers.

An insert in accord with the inventive concepts may be either formed of metal, an elastomer or a synthetic plastic material. In one metal version, the deformable malleable fingers are utilized on one of the lateral sides of the insert while the crescent shaped extensions are employed on the other insert side. In a synthetic or plastic version of the retainer, deformation by squeezing of the fingers permits the associated protuberances defined on the fingers to slide between and behind the tiewings so when the pressure is relieved, they spring behind the tiewings and lock to engage. Once again the other lateral side is secured by sliding the crescent shaped extensions behind the tiewings.

If the insert is formed of a stretchable elastomeric material, both of the lateral anchors may be of the elongated crescent shaped extension configuration wherein stretching and distortion of the insert during assembly to the bracket is possible and permits use of the extensions.

The invention will fit both generic and preadjusted twin edgewise brackets. It is an insert that is placed in the longitudinal space between the two tiewings of a twin edgewise bracket. The device secures to place by having the curved extensions of the main member at one end of the insert slide behind the tie wings on one side and, depending on the material from which it is manufactured, having the other side either bent, squeezed and placed, or stretched behind the opposing tiewings.

The device, because of these self-locking designs, eliminates the need for ligatures, thereby reducing friction. However, since the design also features mesio-distal (horizontal) extensions of the slot cover over the archwire slot, ligatures or Kobayashi ties (a form of metal ligature which includes a formed hook), or elastomeric power chain can be used with the device. However, these ancillary mechanisms will not touch the archwire, once again reducing friction dramatically. The thickness of the device between the tiewings creates a shoulder that lifts the slot cover so that it does not constantly touch the archwire, yet contains the archwire in the archwire slot and does not allow it to escape. The crescent shape of the curved extensions behind the tiewings allow ample room for the ligature or other auxiliary device to be placed.

The elastomeric version of the device can be formed with joining links of elastomeric material thereby making a chain of units that would apply force when stretched to move teeth. By making the device in a chain, it eliminates the need of placing individual devices and putting a chain on top of them.

The device does not have a locked or unlocked position. The device is either secured on the bracket or taken completely off the bracket. During treatment, the device may or may not be used, at the discretion of the practitioner. When not used, the twin edgewise bracket can be ligated with a conventional ligature. In some cases, the device will be used on certain teeth and not on others, once again at the discretion of the practitioner. The twin edgewise bracket does not have to be altered or redesigned in order to use the device. The device is designed to fit twin edgewise brackets.

The device will lessen overall treatment time because teeth will move more quickly due to less friction. The device will reduce the number of office visits during treatment because the device does not have to be changed as often as elastomeric ligatures, and the reduced friction will enhance a smooth tooth movement. The device will allow the practitioner to reevaluate the anchorage requirements for certain cases because of reduced force needed to move teeth. The device will allow the practitioner additional treatment options since the device can be placed on or taken off each edgewise bracket at any time during treatment.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENTS

Figure 1:
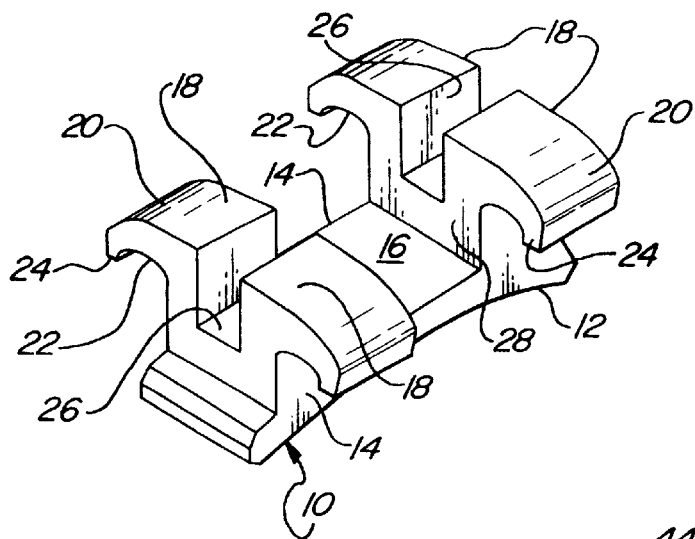
FIG. 1 is a perspective view of a typical edgewise orthodontic bracket with which the insert of the invention is employed.

A typical twin edgewise orthodontic bracket with which the insert of the invention would be used is illustrated in FIG. 1, and such a bracket includes an elongated generally rectangular body 10 having a concave support surface 12 which is adhered to the tooth to be treated. The body 10 includes a pair of lateral sides 14 and a generally planar central region 16. Four tiewings 18 extend away from the support surface 12 in a manner as will be appreciated from FIG. 1, and the tiewings include extensions 20 which extend beyond the projection of the lateral sides 14. Each of the extensions 20 includes an underside 22 upon which is formed a hook 24 in order to retain a ligature attached to the tiewings.

The body 10 includes an archwire slot 26 which is parallel to the length of the body 10 and is located intermediate opposed lateral tiewings as will be appreciated from FIG. 1. Also, a recess 28 is defined in the body separating the pair of tiewings at each end region of the body wherein the recess 28 is also defined by the surface 16.

Figure 2:
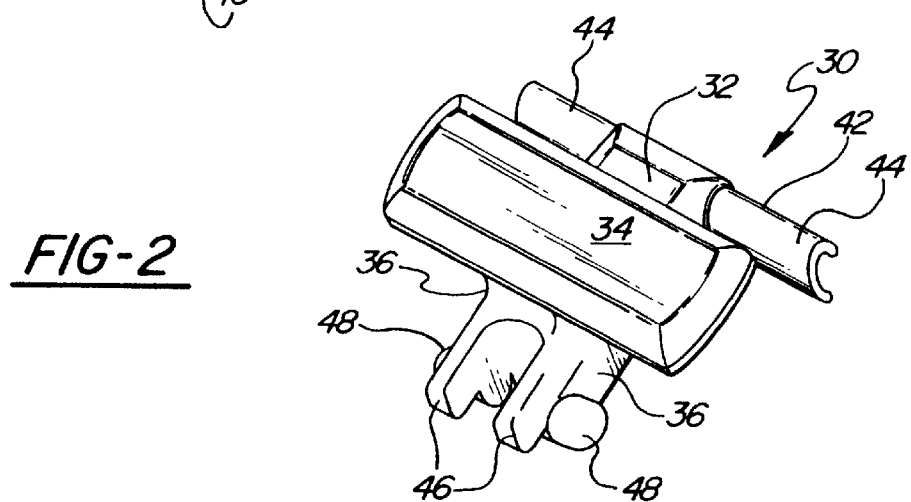
FIG. 2 is a perspective view of an edgewise orthodontic bracket insert constructed in accord with the invention wherein the insert is usually formed of a plastic or stiff synthetic material.
Figure 3:
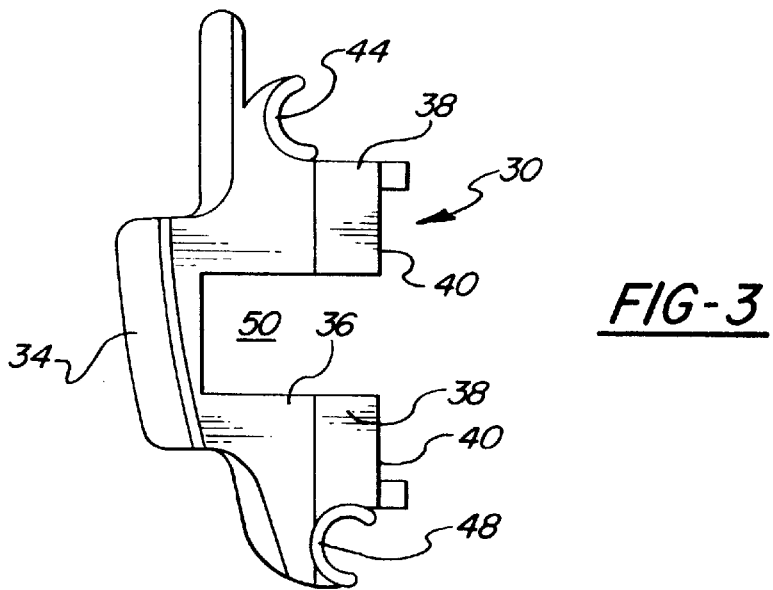
FIG. 3 is an end view of the insert of FIG. 2.
Figure 4:
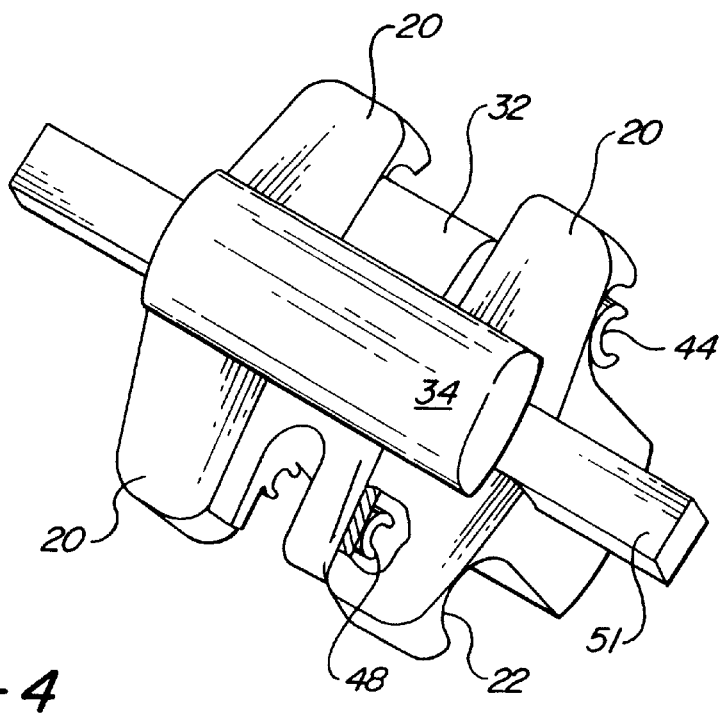
FIG. 4 is a perspective view, partially in section, illustrating an orthodontic bracket and insert when assembled, the insert being of the type shown in FIGS. 2 and 3.

The insert or archwire retainer in accord with the invention which is formed of a stiff plastic or synthetic material at 30, FIGS. 2 and 3, and the insert includes a body 32 having an elongated cap 34 which overlies the bracket body 10 and slightly beyond when the insert is assembled thereto, FIG. 4. The body 32 includes lateral sides 36, and centrally is provided with projections 38 terminating in shoulders 40 for cooperation with the bracket surface 16.

One of the insert body ends is provided with an elongated extension 42 having crescent shaped end regions 44. The other end of the body 32 is provided with resilient deformable fingers 46 each of which has a knob or protuberance 48 extending therefrom. The ends of the fingers 46 comprise extensions which permit a plier or similar tool to engage the ends of the fingers 46 for deforming them toward each other during assembly to the bracket body 10 which will receive an archwire 51 located within the bracket slot 26.

The insert body 32 shown in FIGS. 2–4 will normally be cast, extruded or molded wherein all of the components thereof are of a homogeneous construction. When using the insert 30, the archwire 51 is located within the bracket slot 26 and the insert body 32 is placed upon the bracket body 10 such that the projections 38 are received within the body recess 28 and the insert archwire groove 50 will be in alignment with the bracket body slot 26 such that the archwire 51 will be located within slot 26 and groove 50. The shoulders 40 will be engaging the bracket body central surface 16.

When assembling the insert 30 to the body 10, the crescent shaped extensions slide behind and under two of the tiewing extensions 20 located at a common end of the bracket body, FIG. 4. As the end regions 44 engage the bracket tiewing undersides 22, the insert will slide to the floor of the tiewing undersides and stop. The practitioner will deflect the fingers 46 toward each other by a plier-like instrument, not shown, so that the fingers 46 and protuberances 48 will pass between the two tiewings 18 located on the other end of the bracket body 10. The fingers must be deformed inwardly sufficiently to permit the protuberances 48 to pass between the adjacent tiewings and upon the protuberances 48 being aligned with the adjacent tiewing undersides 22, the fingers are released and will spring away from each other locating the protuberances 48 under the associated tiewing undersides 22 maintaining the insert 30 mechanically connected to the bracket body 10. This relationship is shown in FIG. 4 and the archwire 51 will be located within the body slot 26 and the insert groove 50 in a non-binding relationship to the body 10 and insert 30.

When it is desired to remove the insert 30 from the body 10, the finger end extensions are gripped and biased toward each other to remove the protuberances 48 from under the associated tiewings 18 and the insert may then be slid toward the opposite tiewings until the crescent shaped extensions can be lifted from the body 10.

Figure 5:
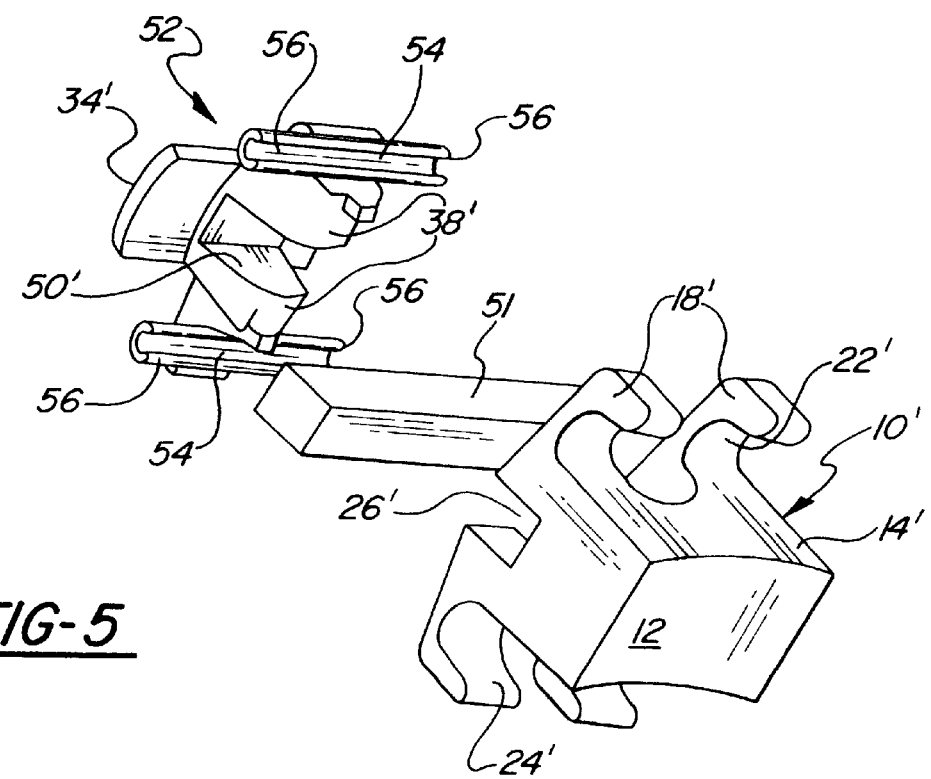
FIG. 5 is an exploded perspective view of an orthodontic bracket, an elastomeric insert and an archwire prior to assembly of the components.
Figure 6:
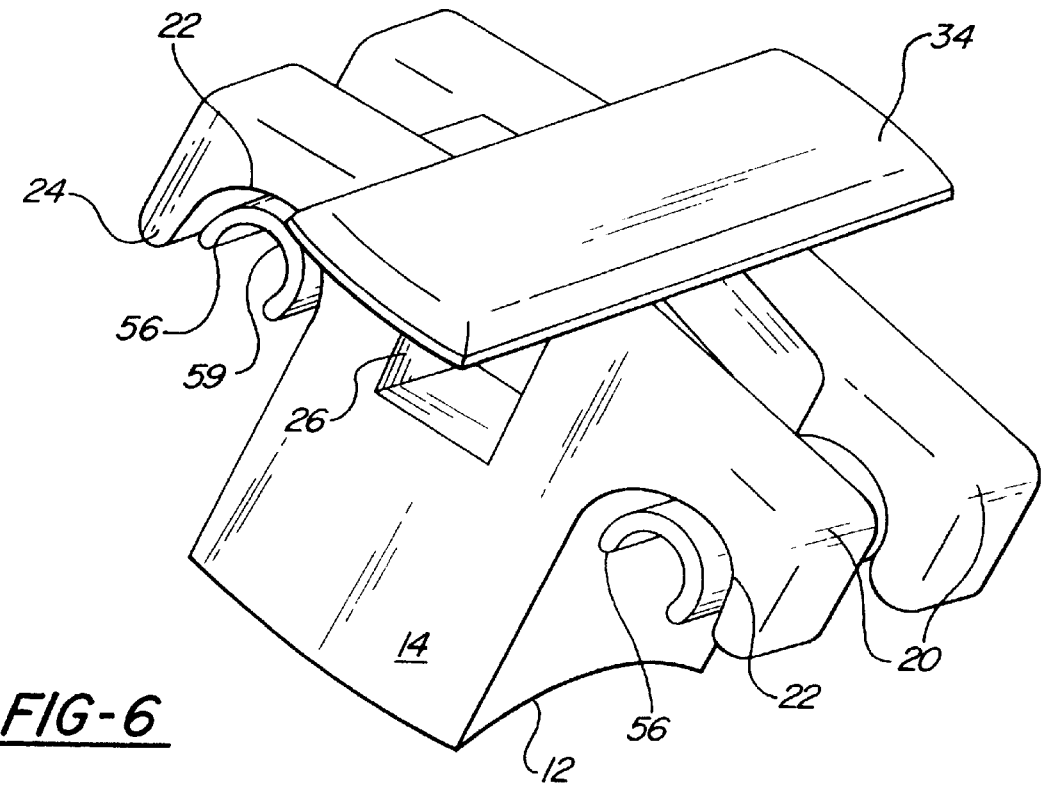
FIG. 6 is a perspective view of an elastomeric insert as used with a typical edgewise orthodontic bracket, the end regions of the crescent shaped extension anchors being located concentric with the underside of the bracket tiewings.

An insert for use with the orthodontic bracket body 10 may be molded of an elastomeric material which is stretchable, and yet has sufficient mechanical characteristics to properly locate the archwire upon the orthodontic bracket. Such an insert 52 is illustrated in FIGS. 5 and 6, and in these figures, elements similar to those previously described are indicated by primed reference numerals.

The insert 52 includes lateral sides, and at each lateral side, a generally crescent shaped elongation 54 is defined, preferably homogeneously molded thereon. The extensions 54 include crescent shaped end regions 56 as will be appreciated from FIG. 5. To assemble the insert 52 upon the bracket body 10', one of the extensions is located under the tiewings 18', and thereupon, the insert 52 is "stretched" sufficiently to locate the other extension 54 over the tiewings located at the other side of the bracket body 10' such that the crescent shaped ends 56 can be placed over the other tiewings for cooperation with the tiewing undersides 22' as will be apparent in FIG. 6. Accordingly, it will be appreciated from FIG. 6, the stretchable resilient nature of the insert 52 permits the anchor extensions 54 to be located under the tiewings 18', and a firm mechanical interconnection between the insert 52 and the body 10' can be achieved. The crescent shaped extension ends including crescent concave grooves 59 allow for maximum room to fit another auxiliary behind the tiewing area while the insert is in place. Disassembly only requires the stretching of the insert sufficiently to withdraw the anchor extension crescent shaped ends 56 of one of the extensions from under the tiewings 18'.

Figure 7:
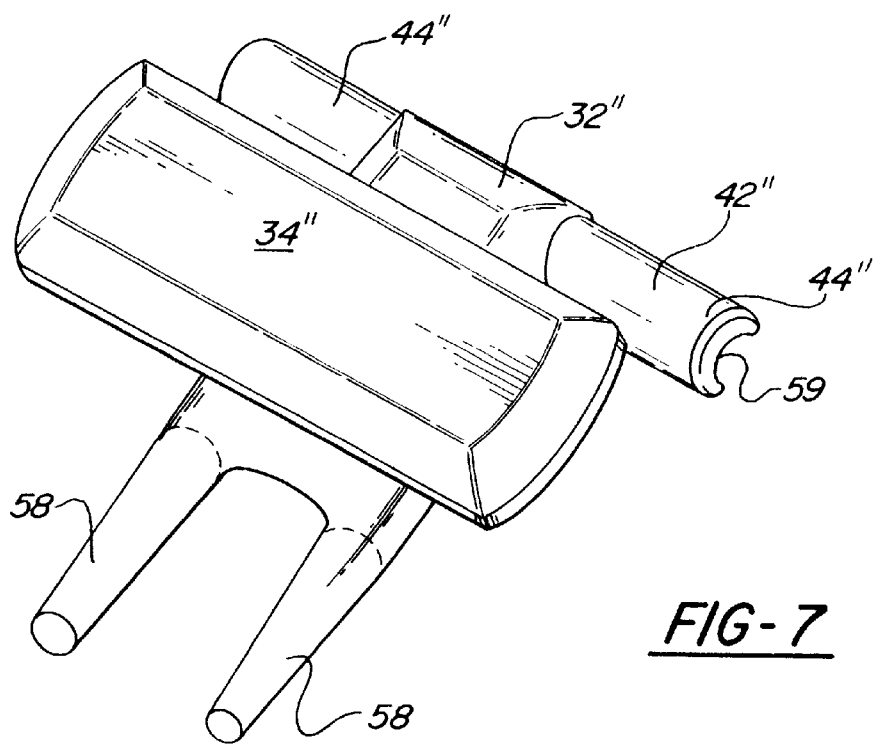
FIG. 7 is a perspective view of a metal insert in accord with the invention having malleable deformable fingers.

FIG. 7 illustrates a malleable metal version of the insert or retainer wherein components similar to those previously described are indicated by double primed reference numerals. The embodiment of FIG. 7 is preferably cast of a malleable metal and includes a cap 34", a body 32" and an extension having crescent shaped end regions 44". Retention of the body 32" upon the body of the bracket 10 is achieved by the malleable fingers 58" extending from the opposite side of the cap 34" as compared to the extension. The fingers are preferably of a cylindrical configuration, and as the fingers are homogeneously formed during the casting of the body 32", the fingers 58 may be readily deformed by the use of pliers to underlie the tiewing extensions 20 to engage the extension undersurfaces 22, and in this manner, the body 32" will be firmly mounted upon the pad body 10.

Figure 8:
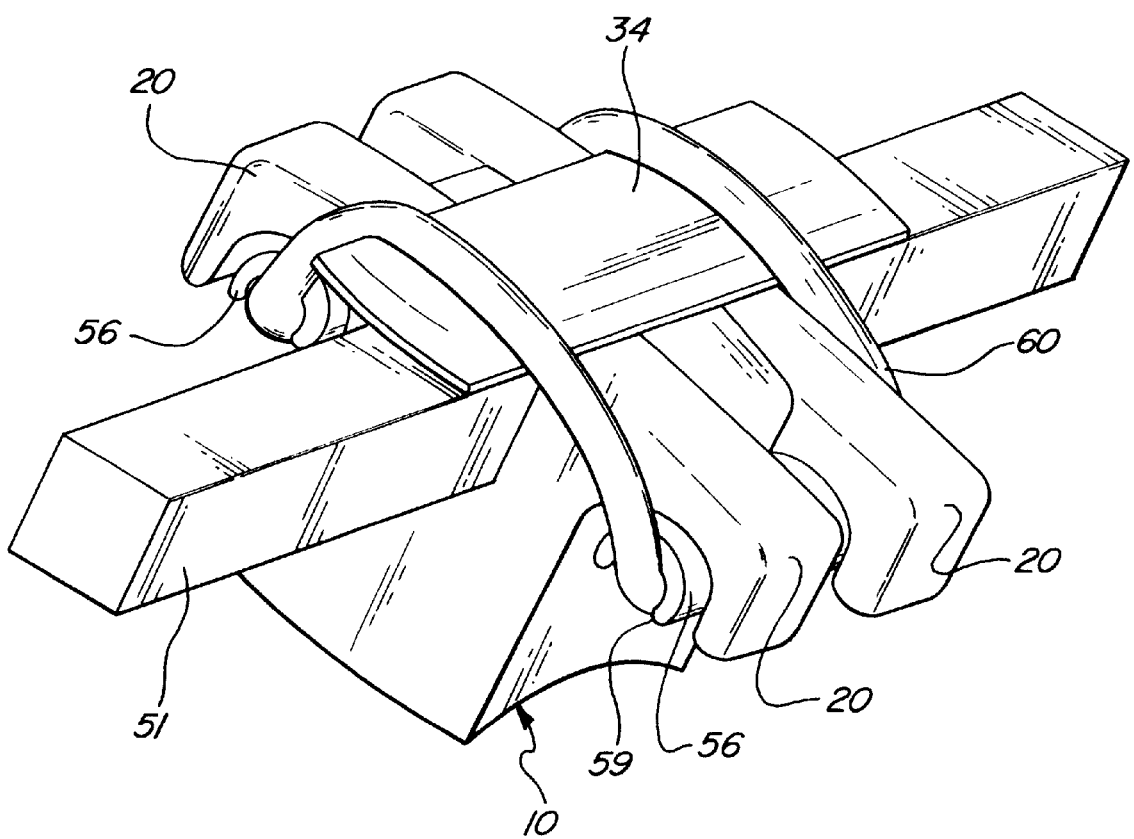
FIG. 8 is a perspective view of a typical edgewise orthodontic bracket with an archwire in the archwire slot, secured in place by a ligature.

FIG. 8 illustrates the use of the inventive concepts wherein, in addition to the normal relationship of components to hold the insert body 32 in place, a flexible or steel ligature 60 is used to additionally maintain the insert body 32 on the bracket body 10. The ligature 60 may be formed of wire, or an elastic band, and as will be appreciated from FIG. 8, the crescent shaped grooves 59 within the extensions 42 permit the ligatures to be maintained in their proper relationship.

The insert of the invention reduces the overall treatment time for straightening teeth because the teeth will move more quickly due to the reduction in friction as compared with known orthodontic devices. The device reduces the number of office visits during treatment because the insert does not have to be changed as often as elastomeric ligatures, and the invention allows the practitioner to re-evaluate anchorage requirements for certain cases, because of reduced force needed to move teeth. The invention allows the practitioner additional treatment options since the insert can be placed on or taken off each bracket at any time during treatment. The practitioner can continue to use conventional edgewise brackets and does not have to change the appliance specifications in order to use the invention.

It is appreciated that various modifications to the inventive concepts may be apparent to those skilled in the art without departing from the spirit and scope of the invention.

What is claimed is:

1. In combination with a conventional unmodified twin edgewise orthodontic bracket, having an elongated pad body having an axis, an inner support surface for engaging the tooth, an outer surface, spaced lateral sides, ends, a central region and a pair of spaced tiewings extending outwardly from each lateral side from said outer surface adjacent said ends and located on opposite sides of said axis, said tiewings including extension portions extending beyond said body sides and each said portion having an underside disposed toward said body inner support surface having a hook configuration defining an indentation, an archwire slot defined on said body parallel to said axis located intermediate tiewings located on opposite sides of said axis, a recess defined in said body transverse to said axis and separating the tiewings located on a common lateral side the improvement comprising, an archwire retainer insert received within the recess having a cap overlying the archwire slot, said insert having first and second lateral anchors engaging said extension portions' undersides and shoulders engaging the body recess to position the insert cap over the archwire in a non-binding relationship, said insert including deformable portions permitting said insert to be deformed to permit said anchors to be received within the tiewing extensions' indentations.

2. In a combination as in claim 1, said retainer insert including a central portion received within said slot having a pad overlying an archwire received within said slot.

3. In a combination as in claim 1, said archwire retainer insert being formed of metal and said anchors being deformable.

4. In a combination as in claim 3, said anchors comprising cylindrical fingers.

5. In a combination as in claim 1, said archwire retainer insert being formed of a stretchable elastomeric material whereby said insert may be stretched to pull said anchors over the tiewings for engaging said extension portions' undersides.

6. In a combination as in claim 1, at least one of said retainer anchors comprising an elongated extension having end portions, said end portions engaging said extension portions' undersides.

7. In a combination as in claim 6, both said first and second anchors comprising elongated extensions each having end portions.

8. In a combination as in claim 6, said first retainer anchor comprising a pair of resilient fingers, and a protuberance defined upon each finger adapted to extend under and engage an extension portion underside.

9. In a combination as in claim 6, said extension end portions being of a crescent shaped configuration.

10. In a combination as in claim 1, said archwire retainer insert being formed of a synthetic material.

11. An insert for use with a conventional twin edgewise orthodontic bracket comprising a body having an axis and having a central cap for overlying an archwire, first and second lateral sides defined on said body on opposite sides of said axis, first and second bracket anchors defined on said first and second sides, respectively, at least one of said anchors comprising a deformable finger having a length extending transversely to said axis, said finger being deformable to engage the underside of the tiewings of a conventional twin edgewise orthodontic bracket.

12. In an insert for use with a conventional twin edgewise orthodontic bracket as in claim 11, said finger being malleable and maintaining the deformation applied thereto.

13. In an insert for use with a conventional twin edgewise orthodontic bracket as in claim 11, at least one of said anchors comprising a pair of deformable fingers, said fingers being resiliently deformable, and a detent protuberance defined upon each finger adapted to engage the underside of a bracket tiewing upon said finger being temporarily deformed toward each other and released.

14. In an insert for use with a conventional twin edgewise orthodontic bracket as in claim 11, said insert body having an inner side, the other of said anchors comprising an extension having a C-shaped transverse cross-section defining an opening extending toward said insert body inner side.

* * * * *